United States Patent [19]

Uriyu et al.

[11] Patent Number: 5,589,516
[45] Date of Patent: Dec. 31, 1996

[54] LIQUID PREPARATION OF ANTITHROMBIN-III AND STABILIZING METHOD THEREFOR

[75] Inventors: Katsuhiro Uriyu; Akimasa Ohmizu; Hajime Fukuyama; Kazuo Takechi; Kazumasa Yokoyama, all of Hirakata, Japan

[73] Assignee: The Green Cross Corporation, Osaka, Japan

[21] Appl. No.: 351,268

[22] PCT Filed: Apr. 5, 1994

[86] PCT No.: PCT/JP94/00563

§ 371 Date: Dec. 5, 1994

§ 102(e) Date: Dec. 5, 1994

[87] PCT Pub. No.: WO94/22471

PCT Pub. Date: Oct. 13, 1994

[30] Foreign Application Priority Data

| Apr. 5, 1993 | [JP] | Japan | 5-100117 |
| Dec. 24, 1993 | [JP] | Japan | 5-328205 |
| Jan. 21, 1994 | [JP] | Japan | 6-005073 |

[51] Int. Cl.$^6$ .......................... A61K 35/16; A61K 37/18; A61K 37/64; A61K 39/395
[52] U.S. Cl. .......................... 514/2; 424/530; 424/531; 514/21; 514/802; 530/383; 530/393
[58] Field of Search ........................ 424/530, 531; 514/2, 21, 802; 530/383, 393

[56] References Cited

U.S. PATENT DOCUMENTS

| 3,784,479 | 1/1974 | Keil | 252/358 |
| 3,984,347 | 10/1976 | Keil | 252/321 |
| 4,005,044 | 1/1977 | Raleigh | 252/358 |
| 4,021,365 | 5/1977 | Sinka et al. | 252/321 |
| 4,076,648 | 2/1978 | Rosen | 252/358 |
| 4,274,977 | 6/1981 | Koerner et al. | 252/358 |
| 4,297,344 | 10/1981 | Schwinn et al. | 424/101 |
| 4,340,589 | 7/1982 | Uemura et al. | 424/101 |
| 4,388,232 | 6/1983 | Eibl et al. | 260/112 |
| 4,415,559 | 11/1983 | Suzuki et al. | 424/183 |
| 4,440,679 | 4/1984 | Fernandes et al. | 260/122 |
| 4,465,623 | 8/1984 | Chanas et al. | 260/112 |
| 4,510,084 | 4/1985 | Eibl et al. | |
| 4,623,717 | 11/1986 | Fernandes et al. | 260/122 |
| 4,639,489 | 1/1987 | Aizawa et al. | 524/588 |
| 4,656,254 | 4/1987 | Shearer et al. | 530/393 |
| 4,749,740 | 6/1988 | Aizawa et al. | 524/588 |
| 4,877,608 | 10/1989 | Lee et al. | 424/858 |
| 4,978,471 | 12/1990 | Starch | 252/174.15 |
| 4,983,316 | 1/1991 | Starch | 252/174.15 |
| 5,084,273 | 1/1992 | Hirahara | 424/94.6 |
| 5,262,088 | 11/1993 | Hill et al. | 252/321 |
| 5,288,431 | 2/1994 | Huber et al. | 252/548 |
| 5,319,072 | 6/1994 | Uemura et al. | 530/393 |
| 5,385,890 | 1/1995 | Aoyama et al. | 514/21 |

FOREIGN PATENT DOCUMENTS

| 0091802A1 | 10/1983 | European Pat. Off. |
| 0163398A1 | 12/1985 | European Pat. Off. |
| 0217501A2 | 4/1987 | European Pat. Off. |
| 341952 | 11/1989 | European Pat. Off. |
| 0339919 | 11/1989 | European Pat. Off. |
| 0438234 | 7/1991 | European Pat. Off. |
| 0549232A1 | 6/1993 | European Pat. Off. |
| 0551084 | 7/1993 | European Pat. Off. |
| 0590531 | 4/1994 | European Pat. Off. |
| 63132843 | of 0000 | Japan |
| 4108738 | of 0000 | Japan |
| WO93/25652 | 12/1993 | WIPO |

*Primary Examiner*—Shep K. Rose
*Attorney, Agent, or Firm*—Sughrue, Mion, Zinn, Macpeak & Seas

[57] ABSTRACT

A liquid preparation of antithrombin-III (AT-III), comprising an AT-III and an organic acid, a salt thereof, a sugar sulfate or a surfactant as a stabilizer, and a liquid preparation of AT-III, having a pH of 9–10. The preparation of the present invention is stable after long-term preservation and poses no clinical problems in terms of pharmacological effects and safety. The preparation is more advantageous than lyophilized preparations in that it does not require dissolution in injectable distilled water and can be used easily. Accordingly, the preparation is clinically very useful.

32 Claims, 1 Drawing Sheet

LIQUID PREPARATION OF ANTITHROMBIN-III AND STABILIZING METHOD THEREFOR

TECHNICAL FIELD

The present invention relates to a liquid preparation of antithrombin-III, which is stable during a long-term storage, and a method for stabilizing the liquid preparation of antithrombin-III.

BACKGROUND ART

An antithrombin-III (hereinafter referred to as AT-III) is a kind of sugar protein belonging to $\alpha_2$ globulin present in plasma and has a molecular weight of 65,000–68,000. An AT-III has a protease inhibitory activity and shows a strong inhibitory action on coagulation activity of thrombin, as well as an inhibitory action on other blood coagulation factors, activated X factor, activated IX factor and the like. It has been reported that AT-III also shows an inhibitory action on plasmin and trypsin. These inhibitory actions are known to generally proceed faster in the presence of heparin.

An AT-III having such pharmacological actions is used for the correction of abnormally enhanced coagulation, specifically for the treatment of disseminated intravascular coagulation (DIC). AT-III shows poor stability when dissolved and causes side effects in intravenous administration by polymerizing. Accordingly, AT-III has been formulated into lyophilized preparations.

Incidentally, liquid preparations are more advantageous than lyophilized preparations in that they do not require dissolution in injectable distilled water when in use, thus making administration easy, and are produced economically with no need for a freeze-dry step in the production thereof. However, practical formulation of AT-III into liquid preparations has gotten behind due to the poor stability of AT-III in a solution state. There has been only one report in the field of reagent that confirms possible 7 day storage of AT-III in a solution state at 4° C. in the presence of heparin (Japanese Patent Unexamined Publication No. 103463/1980).

DISCLOSURE OF THE INVENTION

An object of the present invention is to improve the stability of AT-III in a solution state and provide a liquid preparation of AT-III, which permits a long-term storage, stability during a long-term storage, particularly at a temperature ranging from 4° C. to room temperature, and easy administration thereof. Another object of the present invention is to provide a method for improving the stability of a liquid AT-III preparation during storage.

With the aim of solving the aforementioned problems in the prior art, the present inventors have conducted a wide range of studies regarding stabilization of AT-III in a solution state, and found that the use of an organic acid, a salt thereof, a sugar sulfate or a surfactant as a stabilizer results in a markedly improved stability of AT-III in a solution state, permitting AT-III to stay stable during a long-term storage. The present inventors have also found that AT-III is extremely stable without a stabilizer in a solution having a pH of 9–10. The present inventors have further found that a liquid AT-III preparation thus prepared poses no clinical problems in terms of pharmacological effect and safety, which resulted in the completion of the invention. It is specifically noted that, while AT-III shows poor stability in a solution of pH 7–8, which is a preferable pH range for injections, the stability thereof in the pH range of 7–8 is remarkably improved by adding the aforementioned compounds as stabilizers.

That is, the present invention relates to:
(1) a liquid preparation of AT-III, comprising an AT-III and an organic acid or a salt thereof;
(2) a liquid preparation of AT-III, which comprises an AT-III and a sugar sulfate and has a pH of 7–10;
(3) a liquid preparation of AT-III, having a pH of 9–10;
(4) a liquid preparation of AT-III, comprising an AT-III and a surfactant;
(5) a method for stabilizing a liquid preparation of AT-III during storage, comprising adding an organic acid or a salt thereof as a stabilizer to a liquid preparation of AT-III;
(6) a method for stabilizing a liquid preparation of AT-III during storage, comprising adding a sugar sulfate as a stabilizer to a liquid preparation of AT-III and adjusting its pH to 7–10;
(7) a method for stabilizing a liquid preparation of AT-III during storage, comprising adjusting its pH to 9–10; and
(8) a method for stabilizing a liquid preparation of AT-III during storage, comprising adding a surfactant to the preparation.

DETAILED DESCRIPTION OF THE INVENTION

(I) AT-III

Figure 1:
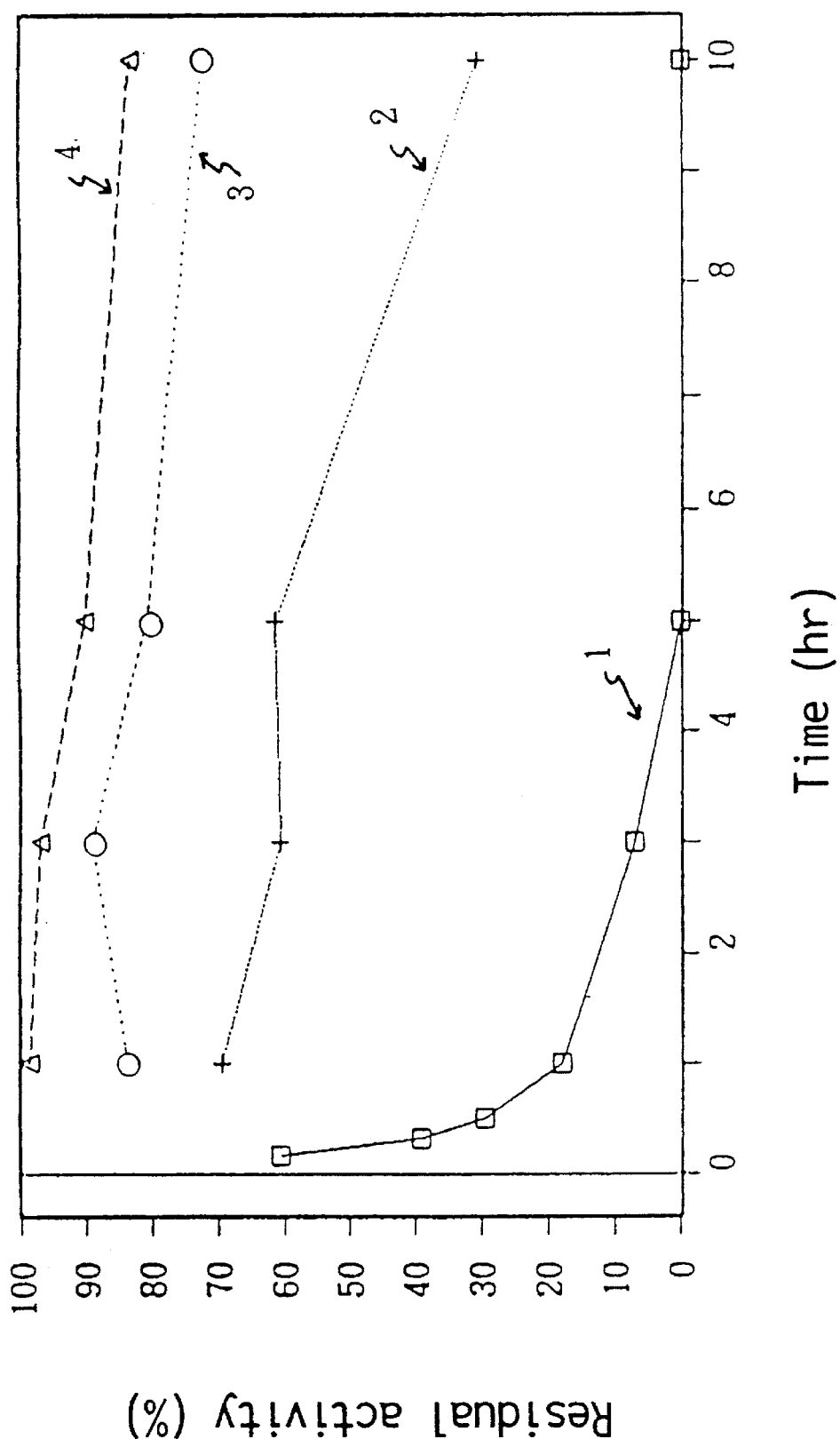
FIG. 1 is a graph showing the results of Experimental Example 3, wherein the stability of AT-III in an aqueous solution prepared by dissolving a lyophilized preparation of AT-III, and the stability of AT-III in a liquid preparation of the present invention were compared. In the FIGURE, 1 is the time course stability of an aqueous solution of a lyophilized preparation of AT-III without stabilizer; 2 is the time course stability of an AT-III solution added with one w/v % sodium citrate and three w/v % sodium aspartate as stabilizers; 3 is the time course stability of an AT-III solution added with one w/v % sodium citrate and three w/v % sodium tartrate as stabilizers; and 4 is the time course stability of an AT-III solution added with one w/v % sodium citrate and three w/v % sodium DL-malate as stabilizers.

The AT-III to be used in the present invention is subject to no particular limitation insofar as it is derived from humans and purified to the degree that permits its use as a medicament. It can be purified from, for example, whole blood, plasma, serum and compressed serum from coagulated blood of humans. The blood to be used preferably tests negative to HB antigens and anti-HIV antibodies and has a GTP of not more than twice the normal value.

The method for purifying AT-III from blood and plasma is, for example, the method disclosed in Japanese Patent Unexamined Publication No. 35017/1973 (U.S. Pat. No. 3,842,061), Japanese Patent Publication No. 7693/1984 (U.S. Pat. No. 4,340,589), Japanese Patent Unexamined Publication No. 275600/1989 (EP 339919) or EP 551084.

For example, low temperature ethanol fraction IV-1, fraction IV or fractions II and III in the supernatant of plasma, after removing cryoprecipitate, may be purified by steps such as heparin affinity chromatography.

In addition, an AT-III prepared by cell culture [e.g., Japanese Patent Application under PCT laid-open under Kohyo No. 500768/1982 (EP 53165)], genetic engineering

[e.g., Japanese Patent Unexamined Publication No. 162529/1983 (EP 90505)] or the like may be used.

(II) LIQUID PREPARATION OF AT-III

The liquid preparation of AT-III of (1) of the present invention comprises an AT-III and an organic acid or a salt thereof, wherein the organic acid is preferably a dibasic acid or citric acid. More preferably, it is a liquid preparation comprising an AT-III, a dibasic acid or a salt thereof, and citric acid or a salt thereof.

In the present invention, an organic acid is a compound having at least 1, preferably 1–3 carboxyl(s) (—COOH) in a molecule. The monobasic acid, dibasic acid and tribasic acid respectively refer to a compound having 1, 2 or 3 carboxyls.

The organic acid to be used in the present invention may be aliphatic or aromatic, saturated or unsaturated, monobasic acid (monocarboxylic acid), dibasic acid (dicarboxylic acid) or tribasic acid (tricarboxylic acid), with preference given to a compound having 2–10, preferably 2–6 carbon atoms. Examples of the monobasic acid include saturated aliphatic monocarboxylic acids such as acetic acid, propionic acid, lactic acid and valeric acid, and monobasic amino acids such as glycine, alanine, valine, leucine and isoleucine. Examples of the dibasic acid include saturated aliphatic dicarboxylic acids such as oxalic acid, malonic acid, succinic acid, glutaric acid and adipic acid, unsaturated aliphatic dicarboxylic acids such as maleic acid and fumaric acid, aromatic dicarboxylic acids such as phthalic acid, dibasic amino acids such as aspartic acid and glutamic acid, and hydroxy dibasic acids such as malic acid and tartaric acid. Examples of the tribasic acid include hydroxy tribasic acids such as citric acid. Preferred are malic acid, tartaric acid, maleic acid, aspartic acid and citric acid.

The organic acid may be a salt. Examples of the salt of the organic acid include alkali metal salts such as sodium salt and potassium salt, alkaline earth metal salts such as calcium salt, and organic salts such as ammonium salt, with preference given to sodium salt.

The organic acid salt to be used in the present invention is more preferably sodium malate or sodium citrate.

It is preferable that the organic acid be a combination of a dibasic acid or a salt thereof, and citric acid or a salt thereof. A combination of a dibasic acid or a salt thereof and citric acid salt is more preferable. Examples of the citric acid salt are alkali metal salts such as sodium salt and potassium salt of citric acid, and alkaline earth metal salts such as magnesium salt and calcium salt of citric acid, with preference given to sodium citrate.

The pH of the liquid preparation of (1) of the present invention is generally 6–10, preferably 7–9, and more preferably 7–8. Preparations having a pH of 7–8 are suitable for injections, since the pain on injection is reduced.

The preparation of (1) of the present invention is a liquid AT-III preparation, which is stable at a pH range of from 6 to 10 and is characterized by being stable during long-term storage, particularly even ill the pH range of 7–8.

The pH can be adjusted by a conventional method and, for example, hydroxides or suitable buffers may be used as adjusting agents. Examples of the hydroxide include sodium hydroxide and potassium hydroxide. Examples of the buffer include phosphate buffer, bicarbonate buffer and Tris buffer.

The liquid AT-III preparation of (1) of the present invention generally comprises an AT-III in a proportion of 1–1000 unit/ml, preferably 1–200 unit/ml, and more preferably 25–100 unit/ml. As used herein, 1 unit of AT-III is the amount corresponding to the amount of AT-III in 1 ml of plasma from a healthy human.

The concentration of the organic acid or a salt thereof to be contained in the liquid preparation is generally 0.1–10 w/v %, preferably 1–5 w/v %, and more preferably 1–3 w/v % in total. When a dibasic acid or a salt: thereof and citric acid or a salt thereof are present as the organic acid, the concentration of the dibasic acid or a salt thereof is preferably 1–5 w/v %, more preferably 1–3 w/v %, and the concentration of citric acid or a salt thereof is preferably 0.5–5 w/v %, more preferably 1–3 w/v %.

The liquid AT-III preparation of (2) of the present invention is characterized in that it comprises an AT-III and a sugar sulfate, and its pH is 7–10.

The sugar sulfate is exemplified by heparin and dextran sulfate, with preference given to heparin.

The liquid AT-III preparation of (2) of the present invention comprises 1–1000 unit/ml, preferably 10–100 unit/ml of AT-III, and 1–1000 unit/ml, preferably 10–100 unit/ml of heparin. The composition ratio of the two is, for example, 0.1–100 units, preferably 1–5 units of heparin per i unit of AT-III.

The pH of the liquid AT-III preparation of (2) of the present invention is 7–10, preferably 8–10. A preparation having a pH 8–10 is preferable in view of the superior stability of AT-III in a solution. The pH may be adjusted by a conventional method using, for example, hydroxides or buffers, as in the preparation of (1) above.

The preparation of (2) of the present invention may comprise the organic acid or a salt thereof as a stabilizer to be used for the preparation of (1) above. The amount of the organic acid or a salt thereof may be determined by reference to the explanation given in this regard for the preparation of (1) above.

The liquid AT-III preparation of (3) of the present invention is characterized in that its pH is 9–10, preferably 9.3–9.8.

The pH may be adjusted by a conventional method using, for example, hydroxides or buffers as in the preparation of (1) above.

The liquid AT-III preparation of (3) of the present invention generally comprises 1–1000 unit/ml, preferably 1–200 unit/ml, and more preferably 25–100 unit/ml of AT-III.

While the liquid AT-III preparation of (3) of the present invention is stable during a long-term storage, even without a stabilizer, it may comprise the organic acid or a salt thereof (e.g., citric acid, citrate and amino acid) to be used for the preparation of (1) above as a stabilizer. The amount of the organic acid or a salt thereof may be determined by reference to the explanation given in this regard for the preparation of (1) above.

The liquid preparation of (4) of the present invention is characterized in that it comprises an AT-III and a surfactant. The addition of a surfactant is conducive to the prevention of insoluble matters which may be developed during storage.

The surfactant is preferably non-ionic and is exemplified by polyoxyethylenesorbitan fatty acid ester (e.g., trademark Tween), polyoxyethylene-polyoxypropylene copolymer (e.g., trademark Pluronic), polyalkylene glycol (e.g., polyethylene glycol and polypropylene glycol) and polyoxyethylene alkyl ether (e.g., trademark Triton). The molecular weight of the surfactant is preferably 2,000–20,000. The fatty acid of the polyoxyethylenesorbitan fatty acid ester is exemplified by fatty acids having 12–18 carbon atoms such as stearic acid, palmitic acid, myristic acid, lauric acid and oleic acid.

Preferably used is polyoxyethylenesorbitan fatty acid ester or polyoxyethylene-polyoxypropylene copolymer.

The liquid AT-III preparation of (4) of the present invention generally comprises 1–1000 unit/ml, preferably 1–200 unit/ml, and more preferably 25–100 unit/ml of AT-III. The concentration of the surfactant is generally 0.01–1 w/v %, preferably 0.01–0.1 w/v %, and more preferably 0.02–0.05 w/v %.

The osmotic pressure of the liquid preparation of the present invention is preferably the same as or close to that of human and animals under physiological conditions.

The liquid preparation of the present invention may comprise pharmaceutically efficacious ingredients other than AT-III insofar as they do not exert adverse influences on the objects of the present invention.

The liquid preparation of the present invention may comprise additives conventionally used for liquid preparations, such as an isotonizing agent (e.g., sorbitol, mannitol, glycerin, polyethylene glycol, propylene glycol, glucose and sodium chloride), an anticeptic-bacteriocidal agent (e.g., benzalkonium chloride, p-hydroxybenzoate, benzyl alcohol, p-chlorometaxenol, chlorocresol, phenetyl alcohol, sorbic acid and a salt thereof, thimerosal and chlorobutanol), a chelating agent (e.g., sodium edetate and condensed sodium phosphate) and a thickener (e.g., polyvinylpyrrolidone, methylcellulose, sodium carboxymethylcellulose, hydroxypropylcellulose, polyvinyl alcohol and sodium polyacrylate) in conventional amounts, as far as they are in line with the objects of the present invention.

Moreover, the liquid preparation of the present invention may comprise a sugar as an auxiliary stabilizer. The sugar to be used in the present invention is, for example, a monosaccharide, a disaccharide, a sugar alcohol or an amino sugar. Examples of the monosaccharide are glucose, fructose, galactose, mannose, arabinose and inositol; examples of the disaccharide are saccharose, lactose and maltose; and examples of the sugar alcohol are mannitol, sorbitol and xylitol. The amino sugar is exemplified by glucosamine and N-acetyl-D-glucosamine which is an amino sugar derivative.

Preferred are saccharose, lactose, sorbitol, inositol, maltose, N-acetyl-D-glucosamine and mannitol.

When a sugar is added, the concentration thereof is generally 0.1–40 w/v %, preferably 0.5–20 w/v %, and more preferably 5–10 w/v %.

The liquid preparations (1) to (3) of the present invention may further comprise a surfactant as an auxiliary stabilizer. The addition of a surfactant results in the prevention of insoluble matters which may be developed during storage. The surfactant is preferably non-ionic and is exemplified by polyoxyethylenesorbitan fatty acid ester (e.g., trademark Tween), polyoxyethylene-polyoxypropylene copolymer (e.g., trademark Pluronic), polyalkylene glycol (e.g., polyethylene glycol and polypropylene glycol) and polyoxyethylene alkyl ether (e.g., trademark Triton). The molecular weight of the surfactant is preferably 2,000–20,000. The fatty acid of the polyoxyethylenesorbitan fatty acid ester is exemplified by fatty acids having 12–18 carbon atoms such as stearic acid, palmitic acid, myristic acid, lauric acid and oleic acid.

When a surfactant is added, the concentration thereof is generally 0.01–1 w/v %, preferably 0.01–0.1 w/v %, and more preferably 0.02–0.05 w/v %.

The liquid preparation of the present invention may contain other stabilizers. Examples thereof are inorganic salts, albumin, aprotinin, ethylenediaminetetraacetic acid (EDTA) and a salt thereof.

The inorganic salt is subject to no particular limitation and is exemplified by sodium chloride, potassium chloride, disodium hydrogenphosphate, sodium dihydrogenphosphate, sodium phosphate, dipotassium hydrogenphosphate, potassium dihydrogenphosphate and potassium phosphate.

The liquid preparation of the present invention is subject to no particular limitation as long as AT-III is dissolved in water along with other ingredients, and it may be an injection, infusion or the like. As the water in which AT-III is dissolved, injectable distilled water, sterile purified water or the like may be used.

The liquid preparation of the present invention can be prepared by a method known per se according to the kind of liquid preparation required. When desired, treatments such as heat treatment and sterilization by filtration may be applied.

The liquid preparation of the present invention thus obtained can be stored for a long time at a temperature from 4° C. to room temperature. Specifically, storage can be at a temperature of not more than 10° C. for at least 2 years and at room temperature for at least 6 months. Preferably, it is stored at a temperature of not more than 10° C.

The liquid preparation of AT-III of the present invention generally shows retention of at least 80%, preferably 90% of the activity of AT-III upon formulation into preparation, even after storage at 25° C. for at least 6 months, preferably at 4° C. for at least 3 years.

The liquid preparation of the present invention is useful for the treatment of thrombophilia induced by the congenital lack of AT-III and disseminated intravascular coagulation (DIC) which is accompanied by a decrease in AT-III.

The administration method of the preparation of the invention is similar to that of conventional AT-III injections and infusions, and is exemplified by slow intravenous injection or intravenous infusion.

The preparation of the present invention is generally administered in 1,000–3,000 units per day (or 20–60 unit/kg), which may be varied according to age, body weight, symptom, etc.

When the preparation is used for an emergency treatment in obstetrical or surgical DIC etc., it is preferably administered in 40–60 unit/kg once a day.

EFFECTS OF THE INVENTION

The liquid preparation of AT-III of the present invention comprising an AT-III and a stabilizer (organic acid or a salt thereof, sugar sulfate or surfactant) is capable of preventing lowering of AT-III activity and polymerizing, during heat treatment and long-term storage.

In accordance with the present invention, moreover, AT-III can be maintained stably for a long time in a liquid state even at pH 7–8, at which range the activity of AT-III has hardly been maintained in conventional preparations.

In addition, the liquid preparation of AT-III of the present invention, having a pH of 9–10, can prevent lowering of AT-III activity and polymerizing, during heat treatment and long-term storage, even without a stabilizer.

The preparation of the present invention is a liquid preparation capable of stably retaining AT-III during a long-term storage. Accordingly, the liquid preparation of the present invention can be provided as it is as a product such as an injection. That is, it is not necessary to dissolve the preparation when in use. The preparation can be directly administered to patients as an injection, etc., thus simplifying its handling for administration, and is clinically useful. Besides, since a freeze-dry step can be eliminated from the production steps, efficient and economical production becomes attainable.

EXAMPLES

The present invention is explained in more detail by illustrative Examples, to which the invention is not limited.

Example 1

An AT-III (500 units), sodium malate (250 mg) and sodium citrate (50 mg) were dissolved in injectable water (5 ml), and the pH was adjusted to 7.5 to yield a liquid preparation of AT-III.

Example 2

An AT-III (500 units), sodium tartrate (250 mg) and sodium citrate (50 mg) were dissolved in injectable water (5 ml), and the pH was adjusted to 7.5 to yield a liquid preparation of AT-III.

Example 3

An AT-III (500 units), sodium aspartate (250 mg) and sodium citrate (50 mg) were dissolved in injectable water (5 ml), and the pH was adjusted to 7.5 to yield a liquid preparation of AT-III.

Example 4

An AT-III (500 units) and sodium aspartate (250 mg) were dissolved in injectable water (5 ml), and the pH was adjusted to 7.5 to yield a liquid preparation of AT-III.

Example 5

An AT-III (500 units), sodium malate (250 mg) and sorbitol (150 mg) were dissolved in injectable water (5 ml), and the pH was adjusted to 8.0 to yield a liquid preparation of AT-III.

Example 6

An AT-III (500 units), sodium malate (250 mg), sorbitol (250 mg) and sodium citrate (50 mg) were dissolved in injectable water (5 ml), and the pH was adjusted to 7.0 to yield a liquid preparation of AT-III.

Example 7

An AT-III (500 units, lyophilized preparation, trademark Neuart manufactured by The Green Cross Corporation) and heparin (1,000 units) were dissolved in injectable water (suitable amount) to make the total amount 20 ml. Its pH was adjusted to 8 to yield a liquid preparation of AT-III.

Example 8

An AT-III (500 units), sodium chloride (50 mg), sodium citrate (52 mg), mannitol (200 mg) and heparin (500 units) were dissolved in injectable water (20 ml), and the pH was adjusted to 8 to yield a liquid preparation of AT-III.

Example 9

An AT-III (500 units, lyophilized preparation, trademark Neuart manufactured by The Green Cross Corporation) was dissolved in injectable water (20 ml), and the pH was adjusted to 9 to yield a liquid preparation of AT-III.

Example 10

An AT-III (500 units, lyophilized preparation, trade mark Neuart manufactured by The Green Cross Corporation) was dissolved in injectable water (20 ml), and the pH was adjusted to 10 to yield a liquid preparation of AT-III.

Example 11

An AT-III (500 units, lyophilized preparation, trademark Neuart manufactured by The Green Cross Corporation) and saccharose (200 mg) were dissolved in injectable water (10 ml), and the pH was adjusted to 9.3 to yield a liquid preparation of AT-III.

Example 12

An AT-III (500 units, lyophilized preparation, trademark Neuart manufactured by The Green Cross Corporation), mannitol (50 mg) and sodium citrate (50 mg) were dissolved in injectable water (10 ml), and the pH was adjusted to 9.8 to yield a liquid preparation of AT-III.

Example 13

An AT-III (500 units) and sodium citrate (250 mg) were dissolved in injectable water (5 ml), and the pH was adjusted to 7.5 to yield a liquid preparation of AT-III.

Example 14

An AT-III (500 units), sodium citrate (250 mg) and saccharose (500 mg) were dissolved in injectable water (5 ml), and the pH was adjusted to 7.5 to yield a liquid preparation of AT-III.

Example 15

An AT-III (500 units), sodium citrate (250 mg) and polyoxyethylene-polyoxypropylene copolymer (2 mg, trademark Pluronic PF68) were dissolved in injectable water (5 ml), and the pH was adjusted to 7.5 to yield a liquid preparation of AT-III.

Example 16

An AT-III (500 units), sodium malate (150 mg), citric acid (150 mg), saccharose (250 mg) and polyoxyethylene-polyoxypropylene copolymer (0.5 mg, trademark Pluronic PF68) were dissolved in injectable water (5 ml), and the pH was adjusted to 7.5 to yield a liquid preparation of AT-III.

The stability of AT-III in the liquid AT-III preparations of the present invention was examined in the following

EXPERIMENTAL EXAMPLES

The stability of AT-III was evaluated on the basis of the residual AT-III activity and/or the ratio of polymerization of AT-III. As noted below, AT-III activity was determined using an AT-III activity determination kit (test team AT-III . 2 kit manufactured by Dai-ichi Kagaku Yakuhin), and the ratio of the polymerized AT-III was determined by HPLC (high performance liquid chromatography) analysis.
(1) Determination of AT-III activity Fifty μl of a dilute sample solution [in 2.4 U/ml heparin, 40 mM Tris-HCl buffer, 0.14M NaCl and 10 mM EDTA (pH 8.4)] was placed in a tube and 100 μl of a human thrombin solution was added [in 0.9% sodium chloride, 0.05% bovine serum albumin (BSA) and 0.05% polyethylene glycol (PEG) 6000; containing 1 U/ml thrombin]. The mixture was pre-incubated at 37° C. for 5 minutes. Then, 100 μl of a synthetic substrate solution (S-2238: HD-phenylalanyl-L-pipecolyl-L-arginyl-p-nitroanilide dihydrochloride) was added thereto, and the mixture was incubated at 37° C. for 5 minutes. After color development, a citric acid solution (1 ml) was added thereto to stop the reaction, and absorbance at 405 nm was measured with a spectrophotometer. Normal human plasma (1U AT-III/ml) was determined concurrently with the sample determination, and AT-III content in the sample was determined from the calibration curves thereof.

(2) HPLC analysis

A G3000 SW$_{XL}$ column (manufactured by Toso) was equilibrated with 0.05M phosphate buffer (pH 7.0) mixed with 0.3M NaCl and analyzed at a flow rate of 0.7 ml/min.

Experimental Example 1

Sodium aspartate (5 w/v %) and 1 w/v % sodium citrate were added to AT-III solutions (AT-III potency: 80.4 U/ml, 0.5% sodium citrate buffer, pH 7.5, 8.0, 8.5 or 9.0), and the mixtures were heated at 55° C. for 30 minutes at a pH ranging from 7.5 to 9.0, followed by determination of residual AT-III activity. The results are shown in Table 1.

In Table 1, control is a sample before the heat treatment, and the residual AT-III activity in each sample was calculated against the AT-III activity of the control (potency: 70.2 U/ml) as 100%.

TABLE 1

Relationship betweeb stabilizer (5 w/v % sodium aspartate and 1 w/v % sodium citrate) and pH

| pH of test solution | residual potency (U/ml) | residual ratio (%) |
|---|---|---|
| 7.5 | 70.5 | 100.4 |
| 8.0 | 70.2 | 99.9 |
| 8.5 | 71.7 | 102.1 |
| 9.0 | 74.3 | 105.8 |
| control | 70.2 | 100 |

As the results show, residual AT-III activity was 99.9% or more at pH 7.5–9, and AT-III was stable.

Experimental Example 2

AT-III solutions (AT-III potency: 80.4 U/ml, pH 7.5) containing various stabilizers (sodium aspartate, sodium glutamate, sodium tartrate or sodium DL-malate) at 3 w/v % or 5 w/v % were prepared. The stability of AT-III with time during heating at 55° C. for 1–10 hours was determined and compared for respective solutions. The results are shown in Table 2.

TABLE 2

| stabilizer | heating time (h) | residual potency (U/ml) | residual ratio (%) |
|---|---|---|---|
| 3% sodium aspartate | 1 | 74.6 | 92.8 |
|  | 3 | 49.7 | 61.8 |
|  | 5 | 39.5 | 49.1 |
|  | 10 | 27.7 | 34.4 |
| 5% sodium aspartate | 1 | 82.4 | 102.5 |
|  | 3 | 73.0 | 90.7 |

TABLE 2-continued

| stabilizer | heating time (h) | residual potency (U/ml) | residual ratio (%) |
|---|---|---|---|
|  | 5 | 67.1 | 83.5 |
|  | 10 | 51.9 | 64.6 |
| 3% sodium glutamate | 1 | 63.8 | 79.4 |
|  | 3 | 38.1 | 47.4 |
|  | 5 | 26.5 | 32.9 |
|  | 10 | 14.6 | 18.1 |
| 5% sodium glutamate | 1 | 85.1 | 105.8 |
|  | 3 | 68.5 | 85.2 |
|  | 5 | 58.3 | 72.5 |
|  | 10 | 41.9 | 52.1 |
| 3% sodium tartrate | 1 | 74.3 | 92.5 |
|  | 3 | 53.6 | 66.6 |
|  | 5 | 47.2 | 58.7 |
|  | 10 | 35.3 | 43.9 |
| 5% sodium tartrate | 1 | 86.8 | 108.0 |
|  | 3 | 81.3 | 101.1 |
|  | 5 | 82.4 | 102.5 |
|  | 10 | 64.5 | 80.2 |
| 3% sodium malate | 1 | 86.0 | 107.0 |
|  | 3 | 75.4 | 93.8 |
|  | 5 | 70.2 | 87.3 |
|  | 10 | 53.0 | 66.0 |
| 5% sodium malate | 1 | 95.1 | 118.3 |
|  | 3 | 84.0 | 104.5 |
|  | 5 | 76.2 | 94.8 |
|  | 10 | 70.2 | 87.3 |
| not heated | — | 80.4 | 100 |

Experimental Example 3

Sodium aspartate, sodium tartrate or sodium DL-malate was added to a purified AT-III solution (1.0% sodium titrate, pH 7.5, AT-III potency: 85.9 U/ml) to 3 w/v %, and the stability of AT-III with time during heating at 55° C. for 1–10 hours was determined and compared. As a control, the stability of AT-III was examined with respect to an aqueous solution (0.25% sodium chloride, 0.26% sodium citrate, 1% mannitol) of a commercially available lyophilized preparation of AT-III. The results are shown in Table 3 and FIG. 1.

TABLE 3

| stabilizer | heating time | residual potency (U/ml) | residual ratio (%) |
|---|---|---|---|
| not added | 10 min | 51.9 | 60.6 |
| Solution of | 20 min | 33.5 | 39.0 |
| lyophilized | 30 min | 25.3 | 29.5 |
| AT-III | 1 h | 15.3 | 17.8 |
| preparation | 3 h | 5.8 | 6.8 |
|  | 5 h | −1.3 | 0 |
| 1% sodium citrate-3% sodium aspartate | 1 h | 59.5 | 69.3 |
|  | 3 h | 52.0 | 60.6 |
|  | 5 h | 52.6 | 61.2 |
|  | 10 h | 26.3 | 30.6 |
| 1% sodium citrate-3% sodium tartrate | 1 h | 71.7 | 83.5 |
|  | 3 h | 75.6 | 88.0 |
|  | 5 h | 69.5 | 80.9 |
|  | 10 h | 62.0 | 72.2 |
| 1% sodium citrate-3% sodium malate | 1 h | 84.7 | 98.6 |
|  | 3 h | 83.3 | 97.0 |
|  | 5 h | 77.2 | 89.9 |
|  | 10 h | 71.4 | 83.1 |
| not heated | — | 85.9 | 100 |

In the aqueous solution of a lyophilized preparation of AT-III, AT-III was inactivated to 18% by heating at 55° C. for 1 hour, whereas the solutions containing stabilizers retained about 70–100% of AT-III activity. In particular, when 1 w/v % sodium citrate and 3 w/v % sodium DL-malate were added, AT-III retained 80% or more of its activity after heating at 55° C. for 10 hours, indicating an enhanced stabilizing effect of about 60 times or more than in the aqueous solution of the conventional product (lyophilized preparation).

Experimental Example 4

Sodium malate, sodium citrate and a sugar were added to an AT-III solution (AT-III potency: 113.4 U/ml), and the pH of the mixture was adjusted to 7.5. The mixture was subjected to heating at 55° C. for 10 hours, and the effect of the concurrent use of a sugar was examined by measuring the residual AT-III activity after the heat treatment. The results are shown in Table 4. The residual ratio of AT-III activity in each sample was calculated relative to the AT-III activity (potency: 113.4 U/ml) of the sample before the heat treatment, which was taken as 100%.

TABLE 4

| stabilizer | residual potency (U/ml) | residual ratio (%) |
| --- | --- | --- |
| 1% sodium malate-5% sodium citrate-10% saccharose | 104.2 | 91.9 |
| 2% sodium malate-5% sodium citrate-10% saccharose | 93.6 | 82.5 |
| 3% sodium malate-5% sodium citrate-10% saccharose | 99.4 | 87.6 |
| 3% sodium malate-3% sodium citrate-10% saccharose | 103.4 | 91.2 |
| 4% sodium malate-3% sodium citrate-10% saccharose | 113.1 | 99.7 |
| 5% sodium malate-3% sodium citrate-10% saccharose | 112.9 | 99.5 |
| 3% sodium malate-3% sodium citrate-10% sorbitol | 109.2 | 96.3 |
| 3% sodium malate-3% sodium citrate-10% mannose | 83.0 | 73.2 |
| 3% sodium malate-3% sodium citrate-10% fructose | 73.2 | 64.5 |
| 3% sodium malate-3% sodium citrate-10% glucose | 97.4 | 85.9 |
| 3% sodium malate-3% sodium citrate-10% lactose | 105.2 | 92.8 |
| 3% sodium malate-3% sodium citrate-10% inositol | 109.7 | 96.7 |
| 3% sodium malate-3% sodium citrate-10% maltose | 105.2 | 92.8 |
| 3% sodium malate-3% sodium citrate-10% mannitol | 110.2 | 97.2 |

Experimental Example 5

Sodium citrate (0.5 w/v %) and a stabilizer (sodium aspartate, sodium glutamate, sodium tartrate, sodium DL-malate, glycine or sodium acetate) were added to an AT-III solution (AT-III potency: 85.9 U/ml, pH 7.5), and the mixture was heated at 55° C. for 1–10 hours. The stabilizing effect of the various stabilizers and 0.5 w/v % sodium citrate on the AT-III was examined by determining the produced polymer by HPLC. The results are shown in Table 5.

In Table 5, ⊚ means that the polymer content was less than 2%, ○ means that the content was 2–5%, ▲ means that the content was 5–10% and x means that the content was not less than 10%.

TABLE 5

| | Heating time (h) | | | |
| --- | --- | --- | --- | --- |
| Stabilizer | 1 | 3 | 5 | 10 |
| 5% sodium aspartate-0.5% sodium citrate | ⊚ | ○ | ○ | ○ |
| 5% sodium glutamate-0.5% sodium citrate | ○ | ○ | ○ | ○ |
| 5% sodium tartrate-0.5% sodium citrate | ⊚ | ⊚ | ⊚ | ○ |
| 3% sodium DL-malate-0.5% sodium citrate | ⊚ | ○ | ○ | ○ |
| 5% sodium DL-malate-0.5% sodium citrate | ⊚ | ⊚ | ⊚ | ⊚ |
| 5% glycine-0.5% sodium citrate | ▲ | x | | |
| 3% sodium acetate-0.5% sodium citrate | ○ | ▲ | x | |
| not heated | ⊚ | | | |

When a dibasic acid and citric acid were combined for use as the stabilizer, it resulted in inhibited polymerization of AT-III, exhibiting high stabilizing effect.

Experimental Example 6

Sodium aspartate (3 w/v %), 3 w/v % sodium tartrate or 3 w/v % sodium malate was added to AT-III solutions (pH 7.5) as a stabilizer to prepare test solutions. The solutions were respectively heated at 55° C. for 1–10 hours, and residual potency of AT-III was examined.

As a result, high stabilizing effect on AT-III was confirmed in the order of 3 w/v % sodium malate, 3 w/v % sodium tartrate and 3 w/v % sodium aspartate, as compared with the AT-III solution without a stabilizer.

Experimental Example 7

Sodium malate and various stabilizers (glycine, sorbitol and sodium citrate) were added to AT-III solutions (AT-III potency: 125.1 U, pH 7.5) to prepare test solutions (see Table 6). The solutions were stored at 25° C. for 6 months. Six months later, the residual AT-III activity in the samples was measured, the results of which are shown in Table 6.

TABLE 6

| Sample | residual potency (U) | residual ratio (%) |
| --- | --- | --- |
| AT-III-5% sodium malate | 121.9 | 97.5 |
| AT-III-5% sodium malate-1% sorbitol | 123.3 | 98.6 |
| AT-III-3% sodium malate-1% glycine-1% sodium citrate | 117.5 | 93.9 |
| AT-III-3% sodium malate-1% glycine-1% sodium citrate | 124.2 | 99.3 |

Experimental Example 8

Sodium citrate (3.5 w/v %) was added to an AT-III solution (AT-III 100 U/ml), and the pH was adjusted to 7.5 to prepare a liquid preparation of AT-III. The preparation was stored at 40° C. for 1 week or at 25° C. for 1 month, and AT-III activity was measured based on which the residual AT-III activity was determined. The results are shown in Table 7.

TABLE 7

| Stabilizer | storage conditions | residual ratio (%) |
| --- | --- | --- |
| 3.5 w/v % sodium citrate | 40° C., 1 week | 75.2 |
| 3.5 w/v % sodium citrate | 25° C., 1 month | 81.1 |

Experimental Example 9

The stabilizers shown in Table 8 were added to AT-III solutions (AT-III 100 U/ml), and the pH was adjusted to 7.5 to yield liquid preparations of AT-III. These preparations were stored at 40° C. for 1 week, and AT-III activity was measured based on which the residual activity ratio was determined. The results are shown in Table 8.

TABLE 8

| Stabilizer | storage conditions | residual ratio (%) |
| --- | --- | --- |
| 5% sodium citrate | 40° C., 1 week | 87.0 |
| 5% sodium citrate-10% saccharose | 40° C., 1 week | 95.6 |

Experimental Example 10

The stabilizers as shown in Table 9 were added to AT-III solutions (AT-III 100 U/ml), and the pH was adjusted to 7.5 to yield liquid preparations of AT-III. These preparations were stored at 4° C. or 25° C. for 1 month, and AT-III activity was measured based on which the residual activity ratio was determined. The results are shown in Table 9.

TABLE 9

| Stabilizer | storage conditions | residual ratio (%) |
| --- | --- | --- |
| 5% sodium citrate | 4° C., 1 month | 100.0 |
| 5% sodium citrate | 25° C., 1 month | 100.0 |
| 1% sodium citrate-5% glycine | 4° C., 1 month | 100.0 |
| 1% sodium citrate-5% glycine | 25° C., 1 month | 100.0 |
| 5% sodium citrate-10% saccharose | 4° C., 1 month | 100.0 |
| 5% sodium citrate-10% saccharose | 25° C., 1 month | 100.0 |

Experimental Example 11

Sodium citrate (3 w/v %) and 3 w/v % sodium malate were added to AT-III solutions (AT-III 110 U/ml), and the pH was adjusted to 7.5. Polyoxyethylene-polyoxypropylene copolymer (trademark Pluronic PF68) or polyoxyethylene-sorbitan monooleate (trademark Tween 80, manufactured by Wako Pure Chemical Industries, Ltd.) was added in a proportion of 0.01–0.04 w/v % to yield liquid preparations of AT-III. These preparations were shaken at 125 rpm and at 25° C. for 48 hours. Then, the residual AT-III activity was measured and insoluble matter was visually observed. The results are shown in Table 10. In Table 10, ++ means that insoluble matter was observed; ± means that insoluble matter was observed in a slight amount; and − means that insoluble matter was not observed.

The development of insoluble matter was suppressed by the addition of a surfactant.

TABLE 10

| Surfactant | insoluble matters | AT-III activity (%) |
| --- | --- | --- |
| not added | ++ | — |
| 0.01 w/v % Pluronic PF68 | ± | 95.3 |
| 0.02 w/v % Pluronic PF68 | ± | 107.5 |
| 0.04 w/v % Pluronic PF68 | ± | 103.9 |
| 0.01 w/v % Tween 80 | − | 98.4 |
| 0.02 w/v % Tween 80 | − | 97.5 |
| 0.04 w/v % Tween 80 | − | 103.2 |

Experimental Example 12

The relationship between the amount of heparin added to a liquid preparation and stability thereof was examined.

Liquid preparations (pH 7–7.5) containing AT-III at a concentration of 10 U/ml and heparin at a concentration of 0–500 U/ml were heated at 60° C. for 10 minutes at a pH of 7–7.5. As a result, the residual AT-III activity, in the absence of heparin or in the presence of 0.5 U/ml of heparin, was about 5%, whereas it was 18%, 45% or 94% in the presence of 5 U/ml, 50 U/ml or 500 U/ml, respectively, of heparin, thus indicating increased stabilizing effect on AT-III as the heparin concentration increased.

Experimental Example 13

The relationship between the pH of the liquid AT-III preparation of the present invention and the stability of AT-III in the preparation was examined.

Liquid preparations of AT-III (potency of AT-III: 25 unit/ml), which had been adjusted to pH 6, 7, 8, 9 or 10, were heated at 50° C. for 30 minutes. The residual AT-III activity in the respective liquid AT-III preparations was measured, and the stability of AT-III against the heat treatment was compared.

As a result, AT-III in the liquid AT-III preparation (pH 6) was found to be very unstable. However, the residual AT-III activity in the liquid preparations having a pH of 7, 8, 9 or 10 was 52%, 75%, 88% or 92%, indicating extremely superior stability of AT-III when the pH is 9–10, with the higher stability obtained for a higher pH in this range.

Experimental Example 14

The liquid preparations of AT-III (potency of AT-III: 25 unit/ml), which had been adjusted to respective pHs, according to the method of Experimental Example 13, were heated at 55° C. for 30 minutes. Then, the residual AT-III activity in the respective liquid preparations of AT-III was measured.

As a result, AT-III was found to be very unstable at pH 6. However, the residual AT-III activity grew from 24%, 45%, 69% to 84% with the increasing pH of 7, 8, 9 and 10, indicating stability of AT-III in the pH range of 9–10.

REFERENCE EXAMPLE

A paste (10 kg) of fraction IV-1 obtained by Cohn's cold ethanol fractionation was suspended in 100 o of physiological saline, and barium sulfate was added to a concentration of 5 w/v %. The mixture was stirred at room temperature for 30 minutes, and prothrombin present in a slight amount was adsorbed onto barium sulfate and removed. The supernatant thereof was adjusted to pH 6.5, and polyethylene glycol #4000 was added to a concentration of 13 w/v %. The resultant precipitate was removed by centrifugation, and polyethylene glycol #4000 was added to a concentration of 30 w/v %. The resultant precipitate was collected by centrifugation. The precipitate was dissolved in about 20 o of cold physiological saline, and the solution was poured onto a heparin Sepharose column adjusted with physiological saline, in advance, to allow adsorption of AT-III onto the column. The column was washed with a 0.4M sodium chloride solution to remove contaminant protein, and a 2.0M sodium chloride solution was passed through the column, and the eluted portion was recovered.

Sodium citrate was added to said aqueous solution of AT-III to a concentration of 0.6M, and the pH of the mixture was adjusted to 7.8. The mixture was heated at 60° C. for 10 hours and mixed with sodium chloride (final concentration 3M) and sodium citrate (final concentration 20 mM) to adjust the pH to 7.5. The aqueous solution of AT-III was brought into contact with a butyl type polyvinyl carrier (butyl Toyopal 650, manufactured by Toyo Soda) equilibrated with 20 mM sodium citrate buffer (pH 7.5) containing 3M sodium chloride and developed with the above-mentioned buffer to collect an unadsorbed fraction. Then, the fraction was dialyzed overnight against a 0.5% sodium citrate buffer (pH 7.5) to yield a purified AT-III.

What is claimed is:

1. A liquid pharmaceutical preparation of antithrombin-III, comprising an antithrombin-III dissolved in water, an organic acid which is a dibasic acid and/or a tribasic acid or a salt thereof, and a non-ionic surfactant.

2. The preparation of claim 1, wherein the organic acid is a dibasic acid.

3. The preparation of claim 1, wherein the organic acid is citric acid.

4. The preparation of claim 1, comprising an antithrombin-III dissolved in water, a dibasic acid or a salt thereof, citric acid or a salt thereof, and a non-ionic surfactant.

5. A method for stabilizing a liquid preparation of antithrombin-III during storage, comprising adding a sugar sulfate as a stabilizer and adjusting the preparation to pH 7–10.

6. The method of claim 5, wherein the sugar sulfate is heparin.

7. The method of claim 5, comprising adjusting the liquid preparation of antithrombin-III to pH 8–10.

8. The method of claim 6, wherein the antithrombin-III is present at a concentration of 1–1000 unit/ml in the preparation, and the heparin is added at a concentration of 1–1000 unit/ml.

9. The method of claim 8, wherein the antithrombin-III is present at a concentration of 10–100 unit/ml in the preparation.

10. A method for stabilizing a liquid preparation of antithrombin-III during storage, comprising adjusting a liquid preparation of antithrombin-III to pH 9–10.

11. The method of claim 10, comprising adjusting the liquid preparation of antithrombin-III to pH 9.3–9.8.

12. A method for stabilizing a liquid preparation of antithrombin-III during storage, comprising adding a surfactant to a liquid preparation of antithrombin-III.

13. The preparation of claim 1, claim 2 or claim 4, wherein the dibasic acid is at least one member selected from the group consisting of malic acid, tartaric acid, aspartic acid and maleic acid.

14. The preparation of claim 1, wherein the non-ionic surfactant is at least one member selected from the group consisting of polyoxyethylenesorbitan fatty acid ester and polyoxyethylene-polyoxypropylene copolymer.

15. The preparation of claim 1, further comprising a sugar.

16. The preparation of claim 15, wherein the sugar is at least one member selected from the group consisting of saccharose, lactose, sorbitol, inositol, maltose, N-acetyl-D-glucosamine and mannitol.

17. The preparation of claim 1, further comprising a pH-adjusting buffer.

18. The preparation of claim 17, wherein the pH-adjusting buffer is at least one member selected from the group consisting of phosphate buffer, bicarbonate buffer and Tris buffer.

19. The preparation of any one of claims 1 to 4 and 13 to 18, having a pH of 7–8.

20. The preparation of any one claims 1 to 4 and 13 to 19, comprising the organic acid or a salt thereof at a concentration of 0.1–10 w/v % in total.

21. A method of stabilizing, without lyophilization, during a long-term storage, a liquid pharmaceutical preparation comprising an antithrombin-III dissolved in water, which comprises adding an organic acid which is a dibasic acid and/or a tribasic acid or a salt thereof as a stabilizer, and a non-ionic surfactant as an auxiliary stabilizaer to the pharmaceutical liquid preparation.

22. The method of claim 21, wherein the organic acid is a dibasic acid.

23. The method of claim 21, wherein the organic acid is citric acid.

24. The method of claim 21, wherein the stabilizer comprises a dibasic acid or a salt thereof, and citric acid or a salt thereof.

25. The method of any one of claim 21, claim 22 and claim 24, wherein the dibasic acid is at least one member selected from the group consisting of malic acid, tartaric acid, aspartic acid and maleic acid.

26. The method of claim 21, wherein the non-ionic surfactant is at least one member selected from the group consisting of polyoxyethylenesorbitan fatty acid ester and polyoxyethylene-polyoxypropylene copolymer.

27. The method of claim 21, further comprising adding a sugar as an auxiliary stabilizer.

28. The method of claim 27, wherein the sugar is at least one member selected from the group consisting of saccharose, lactose, sorbitol, inositol, maltose, N-acetyl-D-glucosamine and mannitol.

29. The method of claim 21, further comprising adding a pH-adjusting buffer to the liquid pharmaceutical preparation.

30. The method of claim 29, wherein the pH-adjusting buffer is at least one member selected from the group consisting of phosphate buffer, bicarbonate buffer and Tris buffer.

31. The method of any one of claims 21 to 30, comprising adjusting the liquid pharmaceutical preparation to pH 7–8.

32. The method of any one of claims 21 to 31, comprising adding the organic acid or a salt thereof at a concentration of 0.1–10 w/v % in total.

* * * * *